United States Patent
Skjæveland et al.

(10) Patent No.: US 11,815,640 B2
(45) Date of Patent: Nov. 14, 2023

(54) METHOD OF ANALYSING SEISMIC DATA TO DETECT HYDROCARBONS

(71) Applicant: EQUINOR ENERGY AS, Stavanger (NO)

(72) Inventors: Øyvind Skjæveland, Stavanger (NO); Matteo Ravasi, Nesttun (NO)

(73) Assignee: EQUINOR ENERGY AS, Stavanger (NO)

( * ) Notice: Subject to any disclaimer, the term of this patent is extended or adjusted under 35 U.S.C. 154(b) by 137 days.

(21) Appl. No.: 17/413,619

(22) PCT Filed: Dec. 18, 2019

(86) PCT No.: PCT/NO2019/050281
§ 371 (c)(1),
(2) Date: Jun. 14, 2021

(87) PCT Pub. No.: WO2020/130845
PCT Pub. Date: Jun. 25, 2020

(65) Prior Publication Data
US 2022/0057537 A1 Feb. 24, 2022

(30) Foreign Application Priority Data

Dec. 18, 2018 (GB) ..................................... 1820606

(51) Int. Cl.
*G01V 1/30* (2006.01)
*G01N 33/24* (2006.01)

(52) U.S. Cl.
CPC .......... *G01V 1/302* (2013.01); *G01N 33/241* (2013.01); *G01V 1/307* (2013.01); *G01V 2210/1234* (2013.01); *G01V 2210/512* (2013.01); *G01V 2210/632* (2013.01)

(58) Field of Classification Search
CPC ................... G01V 1/302; G01V 1/307; G01V 2210/1234; G01V 2210/512; G01V 2210/632; G01V 2210/645; G01N 33/241
See application file for complete search history.

(56) References Cited

U.S. PATENT DOCUMENTS

| | | | |
|---|---|---|---|
| 5,056,066 | A | 10/1991 | Howard |
| 5,504,678 | A | 4/1996 | Juszczak et al. |
| 5,657,223 | A | 8/1997 | Juszczak et al. |

(Continued)

FOREIGN PATENT DOCUMENTS

| | | | | |
|---|---|---|---|---|
| CA | 3139078 A1 | * | 11/2020 | ........... E21B 49/087 |
| EP | 2 113 796 A1 | | 11/2009 | |

(Continued)

OTHER PUBLICATIONS

International Search Report and Written Opinion, PCT/NO2019/050281, dated Mar. 10, 2020 (7 pp.).

(Continued)

*Primary Examiner* — Mischita L Henson
(74) *Attorney, Agent, or Firm* — Eversheds Sutherland (US) LLP

(57) ABSTRACT

A method of analysing seismic data to detect possible hydrocarbons includes determining a set of data tiles from a seismic data cube of seismic data and testing each data tile in the set of data tiles to determine whether it corresponds to a possible fluid contact.

18 Claims, 10 Drawing Sheets

(56) References Cited

U.S. PATENT DOCUMENTS

| | | | |
|---|---|---|---|
| 6,151,555 A * | 11/2000 | Van Bemmel | G01V 1/34 702/14 |
| 7,203,342 B2 | 4/2007 | Pedersen | |
| 7,463,552 B1 | 12/2008 | Padgett | |
| 8,380,435 B2 | 2/2013 | Kumaran et al. | |
| 8,447,524 B2 * | 5/2013 | Chen | G01V 1/302 702/14 |
| 8,488,409 B2 | 7/2013 | Hill et al. | |
| 10,054,703 B2 | 8/2018 | LeCocq et al. | |
| 10,191,165 B2 | 1/2019 | Vinje | |
| 10,393,899 B2 | 8/2019 | Curry et al. | |
| 2002/0087272 A1 * | 7/2002 | Mackie | G01V 1/303 702/14 |
| 2002/0126896 A1 | 9/2002 | Pedersen | |
| 2011/0002194 A1 | 1/2011 | Imhof et al. | |
| 2013/0064040 A1 * | 3/2013 | Imhof | G01V 1/30 367/73 |
| 2014/0278115 A1 | 9/2014 | Bas et al. | |
| 2015/0316670 A1 | 11/2015 | Kowalik et al. | |
| 2016/0291183 A1 | 10/2016 | Hu et al. | |
| 2018/0126353 A1 | 5/2018 | Zhao et al. | |
| 2018/0321403 A1 * | 11/2018 | Al-Dossary | G06T 15/00 |
| 2019/0345816 A1 * | 11/2019 | Auchere | E21B 44/02 |
| 2020/0278465 A1 | 9/2020 | Salman et al. | |
| 2020/0284936 A1 | 9/2020 | da Silva Ferreira et al. | |
| 2020/0301036 A1 | 9/2020 | Ramfjord et al. | |

FOREIGN PATENT DOCUMENTS

| | | | |
|---|---|---|---|
| GB | 2 400 664 A | | 10/2004 |
| GB | 2 429 526 A | | 2/2007 |
| RU | 26212 U | * | 9/2007 ............... G01V 1/00 |
| WO | 2009/142872 A1 | | 11/2009 |
| WO | 2011/056347 A1 | | 5/2011 |
| WO | 2011/062807 A1 | | 5/2011 |
| WO | 2013/039953 A1 | | 3/2013 |
| WO | 2020/009850 A1 | | 1/2020 |

OTHER PUBLICATIONS

Search Report, GB1820606.0, dated May 30, 2019 (5 pp.).

Extended Search Report for EP19897675.5, dated Jul. 14, 2022 (9 pp.).

Schinelli, Marco, "Using complex seismic attributes to improve 4D visibility of fluids contact movement", SEG Technical Program Expanded Abstract 2006, Jan. 1, 2006 (5 pp.).

Whitcombe, David N., et al., Extended elastic impedance for fluid and lithology prediction, Geophysics, vol. 67, No. 1, p. 63-67, Jan.-Feb. 2002 (5 pp.).

* cited by examiner

METHOD OF ANALYSING SEISMIC DATA TO DETECT HYDROCARBONS

TECHNICAL FIELD

The present invention relates to the field of seismic data analysis. In particular, it relates to a method of analysing seismic data so as to determine possible subsurface locations of hydrocarbons.

BACKGROUND OF THE INVENTION

It is known to analyse seismic AVO (amplitude versus offset) data to search for "fluid contacts", i.e. points in a subsurface reservoir where two different fluids such as oil and water/brine meet. This is important because although the location of a sub-surface fluid reservoir might be known, it might not (otherwise) be known where in the reservoir one type of fluid (e.g. oil) ends, and another (e.g. water or brine) begins, i.e. the location of a fluid contact.

In this regard, it is known to determine the location of fluid contacts in a subsurface reservoir by qualitatively comparing graphical representations of fluid and lithology stacks of seismic data and searching that data, by eye, to identify the locations of relatively large amplitude changes in the fluid stack, which at least partly conform to the structure of the subsurface. Ideally, i.e. to be identified as a fluid contact, these amplitude changes will not be present in the lithology stack. Such amplitude discrepancies can indicate the presence of a fluid contact at those locations. However, this is a time-consuming and labour-intensive process and, moreover, many possible fluid contacts can be missed. Furthermore, it is not economical to analyse all AVO data sets in this way.

SUMMARY OF THE INVENTION

A first aspect of the invention relates to a method of analysing seismic data to determine a possible location of hydrocarbons, the method comprising: determining a set of data tiles from a seismic data cube of seismic data; and testing each data tile in the set of data tiles to determine whether it corresponds to a possible fluid contact.

The invention involves analysing seismic data in a tile-wise manner and testing each tile of seismic data to determine whether it might correspond to a fluid contact. As such, the invention can allow for the location(s) of possible fluid contact(s) to be identified by testing seismic data on a tile-by-tile basis. By testing the seismic data on a tile-by-tile basis, this can allow for a more accurate and, moreover, a quantitative and automated identification process of possible fluid contacts. As the process can be automated, it can be performed, for example, by a computer, with associated improvements in speed, accuracy and cost.

Once a fluid contact has been identified, this may be used to determine a possible location (or boundary) of hydrocarbons. As such, determining a possible location of hydrocarbons preferably comprises determining a possible hydrocarbon boundary, e.g. in a fluid reservoir, from (or corresponding to) a possible location of a fluid contact.

A seismic data cube contains seismic data (amplitude data) as a function of three dimensions, usually two spatial dimensions corresponding to a horizontal position, and one time dimension corresponding to a depth (with greater time corresponding to greater depth).

A data tile is a two-dimensional portion of the seismic data cube, the tile preferably having two spatial dimensions corresponding to horizontal position. The tile may be horizontal or it may be inclined. The tile may be flat. However, it need not necessarily be flat and in some cases it may be curved or uneven.

The seismic data, e.g. from which the seismic data cube is formed, preferably comprises pre-stack seismic data. The seismic data could be old or "legacy" seismic data, e.g. which may have previously been analysed using a different method. Alternatively it could be new seismic data which has not been analysed before. The seismic data could be seismic data obtained, for example, using a standard or known method of AVO seismic data acquisition (e.g. as described below).

The method thus preferably comprises obtaining the seismic data from a memory or acquiring the seismic data with at least one seismic source and at least one seismic receiver array.

The seismic data cube from which the set of data tiles is determined is preferably a seismic data cube suitable for identifying seismic lithology reflections, or lithological boundaries, in the subsurface being analysed. For example, the seismic data cube is may be a lithology cube (e.g. with a $\chi$ angle of around or close to $-45°$, for example from $-30°$ to $-90°$) or a pseudo vp/vs cube (e.g. with a $\chi$ angle of around or close to $45°$, for example from $30°$ to $90°$).

As such, the method may comprise obtaining a seismic data cube (e.g. a lithology cube or pseudo vp/vs cube) suitable for identifying seismic lithology reflections from the seismic data. This can be done, for example, by performing a suitable linear sum of near and far stack seismic data, e.g. as is known in the art.

Using a seismic data cube suitable for identifying seismic lithology reflections can allow the set of data tiles to be determined, the data of which tiles is representative of a lithology change in the subsurface. The set of data tiles preferably comprises tiles which are representative of a lithology change in the subsurface because such tiles are more likely to comprise tiles corresponding to fluid contacts. By determining such a set of data tiles, this means that fewer tiles need to be tested (e.g. compared to a case where all of the possible tiles of seismic data are tested).

The tiles may be identified in the following way. First, a sub-cube may be defined (selected) with the lateral size of a tile. A tile candidate in that sub-cube may be selected, the tile candidate having an associated depth and dip (gradient) (which may be zero, i.e. horizontal, or non-zero, i.e. inclined). All of the traces in the sub-cube are then preferably summed into a single trace along the dip. This may be repeated for all tile candidates in the sub-cube (i.e. all dips and depths). A tile candidate may be confirmed as a tile (i.e. corresponding to a possible boundary) if the sum shows a local amplitude maximum with respect to depth and dips. If confirmed as a tile, the tile may be stored, e.g. in a table, in memory.

Each data tile in the set of data tiles preferably comprises or corresponds to a lateral area of equal to or more than 40 or 49 or preferably more than 400 seismic traces. A data tile may, for example, contain up to 100,000 traces. In a preferred embodiment, each data tile contains 51×51=2601 traces. Such tiles would contain sufficient data to be able to provide a meaningful and useful result. However, they are still small enough to be able to provide a "local" result.

The distance between adjacent traces in a data cube is typically around 12.5 m. However, it could be 6.25 m or 18.75 m or up to 25 m. As such, a tile with 51×51 traces would typically correspond to an area of 625×625 m or 0.4 km². A tile with 7×7 (i.e. 49) traces may have an area of 0.007 km². Tiles may contain traces corresponding to an area of up to 4 km², for example when detecting flatspots. However, the geological structure of the subsurface is not usually planar at this scale. Therefore a tile size from around 0.005 km² to around 5 km² may be preferred and should be a sensible range.

The tiles may be rectangular or square (e.g. corresponding to a rectangular or square array of traces). If so, they preferably comprise an odd number of traces along each edge. This can ensure that there is a trace in the centre position of each tile, which can be beneficial. However, the tiles do not need to be rectangular, and could be circular, elliptical or irregular in shape, for example.

The data tiles in the set of data tiles may be determined by identifying data tiles which correspond to a reflector surface, for example as described in GB 2429526 A. Alternatively or additionally, the data tiles in the set of data tiles may be determined from a dip or azimuth calculation returning a local prevailing dip, as is known in the art.

Preferably, the defined tiles have at least 50% overlap with adjacent tiles and, in some embodiments, close to 100% overlap. For example, in the case of rectangular or square tiles, all but one (or more) column or row of traces may be contained in the next tile along, e.g. in a series or array of tiles. Using such an overlap can help to provide more accurate identification of possible fluid contacts.

The method comprises testing each data tile in the set of data tiles to determine whether each tile corresponds to a possible fluid contact. For example, the seismic data of each data tile may be analysed, e.g. numerically, to provide a value which is indicative of the likelihood of that tile corresponding to (or having a location corresponding to) a fluid contact.

In a preferred embodiment, testing each data tile in the set of data tiles to determine whether it corresponds to a possible fluid contact comprises determining a correlation value, preferably a correlation value between amplitude and time, for each tile. The correlation value could be the Pearson correlation coefficient, or a variant thereof, for example. This correlation coefficient can provide a value which gives a useful indication of whether or not a tile corresponds to a fluid contact.

If the correlation value for a data tile is above a certain threshold (e.g. around 0.7, 0.75, 0.8, 0.85 or 0.9), then that data tile could be identified as possibly corresponding to a fluid contact. That data tile (e.g. data representing its location) could be saved in a memory, e.g. in a table, of data tiles corresponding to possible fluid contacts. The threshold applied could depend on the size of the tile (e.g. number of traces in the tile), for example. For a relatively smaller tile, a higher threshold may be applied than for a relatively larger tile.

Testing each data tile in the set of data tiles to determine whether it corresponds to a possible fluid contact preferably comprises, for each tile: obtaining a plurality of measurements representative of one or more reservoir properties at each of the locations (e.g. trace locations) in the tile (at which seismic data is recorded) or of the average properties in a depth window above and/or below the tile; and calculating the degree of co-variation between a plurality of such measurements and the measured time or depth of the location in the tile. Each of the locations in the tile may mean each of the locations in the tile corresponding to which seismic data (e.g. a trace) is recorded. The measurements representative of reservoir properties could comprise seismic amplitude data such as fluid stack (amplitude) data, for example.

Calculating the degree of co-variation between a plurality of such measurements and the measured time or depth of the tile can provide an indication of whether or not the tile corresponds to a fluid contact. For example, if there is a high degree (e.g. above a certain threshold) of co-variation between a plurality of such measurements and the measured time or depth of the tile, then this can be indicative of a fluid contact.

Preferably, the measurements representative of reservoir properties at each of the locations in the tile or of the average properties in a depth window above and/or below the tile show (e.g. are designed or selected to show) different sensitivity to reservoir fluids.

In some embodiments, the method comprises performing a cluster analysis on the measurements representative of reservoir properties at each of the locations in the tile or of the average properties in a depth window above and/or below the tile to identify how well traces (data) in the data tile can be separated into a plurality of clusters. A cluster analysis may be performed as an alternative to determining a correlation value (e.g. as described above) or in addition to determining a correlation value.

In a cluster analysis, the traces in a tile may be grouped into a plurality of (e.g. two or more) clusters, with each cluster corresponding to a different zone or area of the tile.

A time or depth of each trace may be used as a means to separate the clusters (define the edges or boundaries of the clusters).

The plurality of clusters may consist of two clusters and, in such a case, the time or depth that separates the clusters may correspond to that of a fluid contact.

Alternatively, the plurality of clusters may consist of three clusters and, in such a case, two times or depths may be used to separate the clusters, the two times or depths preferably representing those of a top and a base, respectively, of a transition zone of relatively linear dependency of depth or time and fluid-effect (fluid stack) amplitude.

In some cases, the plurality of clusters may consist of three or more clusters and the times or depths that separate the clusters may correspond to those of a plurality of fluid contacts and/or transition zones.

Performing a cluster analysis to identify how well traces (data) in the data tile can be separated into a plurality of clusters can help with determining whether or not a tile corresponds to a possible fluid contact.

In a cluster analysis, a fluid contact may define a boundary between two clusters. For example, if traces found structurally high clusters together and traces found structurally low clusters together, this could be a way of finding the fluid contact, which is what would divide the clusters. If it is not possible to separate the traces into clusters, then this would be indicative of there probably not being a fluid contact in the tile in question. This method is potentially helpful if the tile is so big that the linear behaviour of amplitude versus time only holds for a small region around the fluid contact (e.g. and does not occur over the whole tile).

Performing a cluster analysis as described above can allow larger tiles to be used, which can provide better statistics than smaller tiles.

The measurements representative of reservoir properties may be from $\chi$ angle rotations. For example, the measurements representative of reservoir properties may be or comprise fluid, lithology and/or pseudo vp/vs data, determined for example, from linear combinations of near and far stack data with different $\chi$ values (e.g. as is known in the art).

The method preferably comprises identifying tiles that show a relatively high co-variation of a fluid-sensitive measurement and the tile time or depth (e.g. greater than around 0.7, 0.75, 0.8, 0.85 or 0.9) and/or a relatively low co-variation of a less fluid-sensitive measurement and the tile time or depth (e.g. less than around 0.4, 0.35, 0.3, 0.25 or 0.2), and preferably both. Identifying tiles that show a relatively high co-variation of a fluid-sensitive measurement and the tile time or depth can provide a useful indication of a tile corresponding to a fluid contact. However, identifying tiles that show both a relatively high co-variation of a fluid-sensitive measurement and the tile time or depth, and a relatively low co-variation of a less fluid-sensitive measurement and the tile time or depth can provide a better indication of a tile corresponding to a fluid contact. Tiles that only show a relatively high co-variation of a fluid-sensitive measurement and the tile time or depth but not a relatively low co-variation of a less fluid-sensitive measurement and the tile time or depth are less likely to correspond to fluid contacts.

The method preferably further comprises applying a filter to identify only tiles that line up with other tiles to form a larger structure above a certain size as corresponding to a possible fluid contact. For example, the method may require finding a plurality of (e.g. two or more) adjacent tiles identified as corresponding to a possible fluid contact for the fluid contact possibility to be kept or saved. The method may require that the plurality of such adjacent tiles covers an area which is at least two times, three times or up to ten or more times the size of a single tile, for example. This can ensure that at least two of the tiles, for example, are statistically independent of each other. The method may additionally or alternatively require that the plurality of such adjacent tiles covers an area which is at least around 3, 3.5, 4, 4.5, 5, 5.5, 6, 6.5 or 7 km, for example.

If an isolated tile is identified as corresponding to a possible fluid contact, such a tile is less likely to actually correspond to a fluid contact as a tile with a plurality of neighbouring tiles also being identified as corresponding to a possible fluid contact. As such, applying such a filter to identify only tiles that line up with other tiles to form a larger structure above a certain size as corresponding to a possible fluid contact can improve the accuracy of the method in identifying fluid contacts.

The method may comprise performing further checks to confirm or increase the confidence with which a fluid contact is identified. For example, the method could comprise performing an optimisation search involving varying, for example, the tile size and/or shape, to find the optimum tile size and/or shape for identifying a fluid contact. In such a method, the tiles could be planar or, alternatively, they could be curved and an optimisation search could involve varying the curvature of the tiles, for example.

As can be appreciated from the above, there are various ways in which a tile may be checked to determine whether or not it corresponds to a fluid contact. These checks may be performed in any order. In some embodiments, all of these checks would be performed. In some embodiments, only a selection (e.g. one or more) or these checked would be performed. In some embodiments, if one or more checks suggest that the tile does not correspond to a fluid contact, then that tile is not identified as corresponding to a possible fluid contact. In some embodiments, a tile must "pass" all checks in order to be identified as corresponding to a possible fluid contact. In some embodiments, a tile must "pass" at least a certain number of checks in order to be identified as corresponding to a possible fluid contact. In some embodiments, one or more checks are designated as "fundamental" checks and if a tile fails one of those fundamental checks then it is not identified as corresponding to a possible fluid contact.

For greater speed and efficiency, the method is preferably performed on, or implemented by, a computer.

The method preferably further comprises outputting and/or storing (e.g. to a screen and/or memory) a set of locations corresponding to possible locations of hydrocarbons (e.g. preferably location(s) of fluid contacts) as determined by the method.

The probability or a measure of the likelihood of each location corresponding to a fluid contact may also be output and/or stored. Such a probability or likelihood may be determined from the determined correlation(s), for example, e.g. using a formula.

The output of the method, e.g. the output set of locations, preferably with a probability or a measure of the likelihood of each location corresponding to a fluid contact, may be used as a basis (optionally in combination with other data that may be available) for deciding whether or not to drill for hydrocarbons at the output set of locations (e.g. at a location within the output set of locations).

In some cases, the method may further comprise drilling for hydrocarbons at at least one of, or at a location within, the output set of locations (e.g. within a region at least partly defined by the output set of locations), as determined by the method. For example, the method may comprise installing a drill (e.g. at least one drill) arranged to drill for hydrocarbons at at least one of, or at a location within, the output set of locations (e.g. within a region at least partly defined by the output set of locations), as determined by the method, and then preferably using (controlling) the drill to drill for hydrocarbons (or check for the presence of hydrocarbons) at that location. The drill may be moved to drill for hydrocarbons at a further location e.g. at a further at least one of, or at a location within, the output set of locations.

A second aspect of the invention relates to a method of prospecting for hydrocarbons comprising performing the method described above (with any of its optional or preferred features) and using an (the) output set of locations in a decision-making process for the drilling of a well.

A third aspect of the invention relates to a computer program product comprising computer readable instructions that, when run on a computer, is configured to cause a processer to perform the method of the first aspect, with any of its optional or preferred features. For example, the invention may relate to a computer program product for analysing seismic data to determine a possible location of hydrocarbons, the computer program product comprising computer readable instructions that, when run on one or more computers, are configured to cause one or more processors to: determine a set of data tiles from a seismic data cube of seismic data; and test each data tile in the set of data tiles to determine whether it corresponds to a possible fluid contact.

The present invention also extends to systems and apparatuses for seismic data analysis. For example, a system may comprise one or more memories and one or more processors configured to perform the method as described above. The one or more memories may store data used as an input to the method (e.g. seismic data) and/or data output from the method (e.g. a set of locations corresponding to possible locations of hydrocarbons (e.g. preferably location(s) of fluid contacts) as determined by the method as described above). The one or more processors may be programmed with software (e.g. computer program(s)) which causes them to perform the method of the present invention. The system may comprise one or more screens and/or data input means, e.g. for a user to control the performing of the method and/or see the output of the method on a screen.

The methods in accordance with the present invention may be implemented at least partially using software e.g. computer programs. It will thus be seen that when viewed from further aspects, the present invention provides computer software specifically adapted to carry out the methods herein described when installed on data processing means (e.g. one or more processors), a computer program element comprising computer software code portions for performing the methods herein described when the program element is run on data processing means, and a computer program comprising code means adapted to perform all the steps of a method or of the methods herein described when the program is run on a data processing system. The data processor may be a microprocessor system, a programmable FPGA (field programmable gate array), etc.

The invention also extends to a computer software carrier comprising such software which when used to operate a processor or microprocessor system comprising data processing means causes in conjunction with said data processing means said processor or system to carry out the steps of the methods of the present invention. Such a computer software carrier could be a physical storage medium such as a ROM chip, RAM, flash memory, CD ROM or disk, or could be a signal such as an electronic signal over wires, an optical signal or a radio signal such as to a satellite or the like.

It will further be appreciated that in some embodiments, not all steps of the methods of the invention need be carried out by computer software and thus from a further broad aspect the present invention provides computer software and such software installed on a computer software carrier for carrying out at least one of the steps of the methods set out herein.

The present invention may accordingly suitably be embodied as a computer program product for use with (or within) a computer system. Such an implementation may comprise a series of computer readable instructions fixed on a tangible medium, such as a non-transitory computer readable medium, for example, diskette, CD ROM, ROM, RAM, flash memory or hard disk. It could also comprise a series of computer readable instructions transmittable to a computer system, via a modem or other interface device, either over a tangible medium, including but not limited to optical or analogue communications lines, or intangibly using wireless techniques, including but not limited to microwave, infrared or other transmission techniques. The series of computer readable instructions embodies all or part of the functionality previously described herein.

Those skilled in the art will appreciate that such computer readable instructions can be written in a number of programming languages for use with many computer architectures or operating systems. Further, such instructions may be stored using any memory technology, present or future, including but not limited to, semiconductor, magnetic, or optical, or transmitted using any communications technology, present or future, including but not limited to optical, infrared, or microwave. It is contemplated that such a computer program product may be distributed as a removable medium with accompanying printed or electronic documentation, for example, shrink wrapped software, preloaded with a computer system, for example, on a system ROM or fixed disk, or distributed from a server or electronic bulletin board over a network, for example, the Internet or World Wide Web.

BRIEF DESCRIPTION OF THE DRAWINGS

Preferred embodiments of the invention will now be described by way of example only and with reference to the accompanying drawings, in which.

DETAILED DESCRIPTION

The present invention relates to a method of analysing seismic data to determine possible subsurface locations of hydrocarbons. The method involves identifying possible locations of fluid contacts, i.e, boundaries between two different fluids such as oil and water/brine, by looking for so-called "fluid effects" in the data. The method is implemented by software, which is configured so as to cause one or more processors to perform the method.

The input to the method is a seismic data set and the output includes a set of locations that a possible (or probable) location of a fluid contact, i.e. a boundary between a hydrocarbon region and another fluid such as water or brine.

The seismic data set can be an existing (already collected) seismic data set or it could be a newly-collected seismic data set. For example, the method can be applied to seismic data sets that have already been analysed (e.g. using a prior art method) to check for any possible fluid contacts or hydrocarbons that had not previously been found.

The method involves defining a set of tiles from a seismic data cube and then testing the seismic data cube tile by tile in order to determine whether each tile is (or might be) associated with or corresponds to a possible fluid effect (i.e. indicating the location of a possible fluid contact). If a tile is identified as corresponding to a possible fluid contact, then the tile is kept and further checks can be performed to confirm (or not) the presence of a fluid contact at that location.

Figure 6:
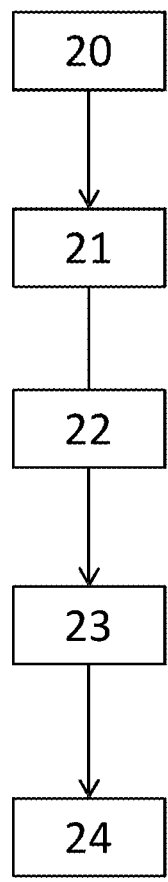
FIG. 6 is a flow chart illustrating a software method of analysing seismic data to determine possible subsurface locations of hydrocarbons.

As illustrated in FIG. 6, the method, which is performed by software, involves the following steps: obtaining seismic data 20; determining a set of tiles to be tested 21; testing those tiles for the presence of a fluid contact 22; performing further checks 23; and saving possible fluid contact candidate tiles 24. These steps 20, 21, 22, 23 and 24 are performed by one or more processors which is/are programmed with suitable software for performing these steps.

The step of obtaining seismic data 20 can mean measuring and recording seismic data (e.g. as described below) or it can mean obtaining it from a memory. In one embodiment, the software is configured to obtain seismic data by measuring and recording seismic data. In an alternative embodiment, the software is configured to obtain seismic data from a memory (or memories).

The step of saving possible fluid contact candidate tiles 24 means storing data related to those tiles in a memory. The software is configured to store data relating to possible fluid contact candidate tiles 24 in a memory. In one embodiment, a set of locations corresponding to possible locations of hydrocarbons (or e.g. preferably location(s) boundaries of fluid contacts) are stored. In another embodiment, the probability or a measure of the likelihood of the location corresponding to a fluid contact is also stored.

As discussed above, the data collection method for the seismic data can be performed just before the analysis of the data with the present invention. Alternatively, the seismic data could have been collected some time in the past and then the analysis method of the present invention applied to it. In either case, it is important to understand the data collection method in order to understand how the data is manipulated and analysed.

Figure 1:
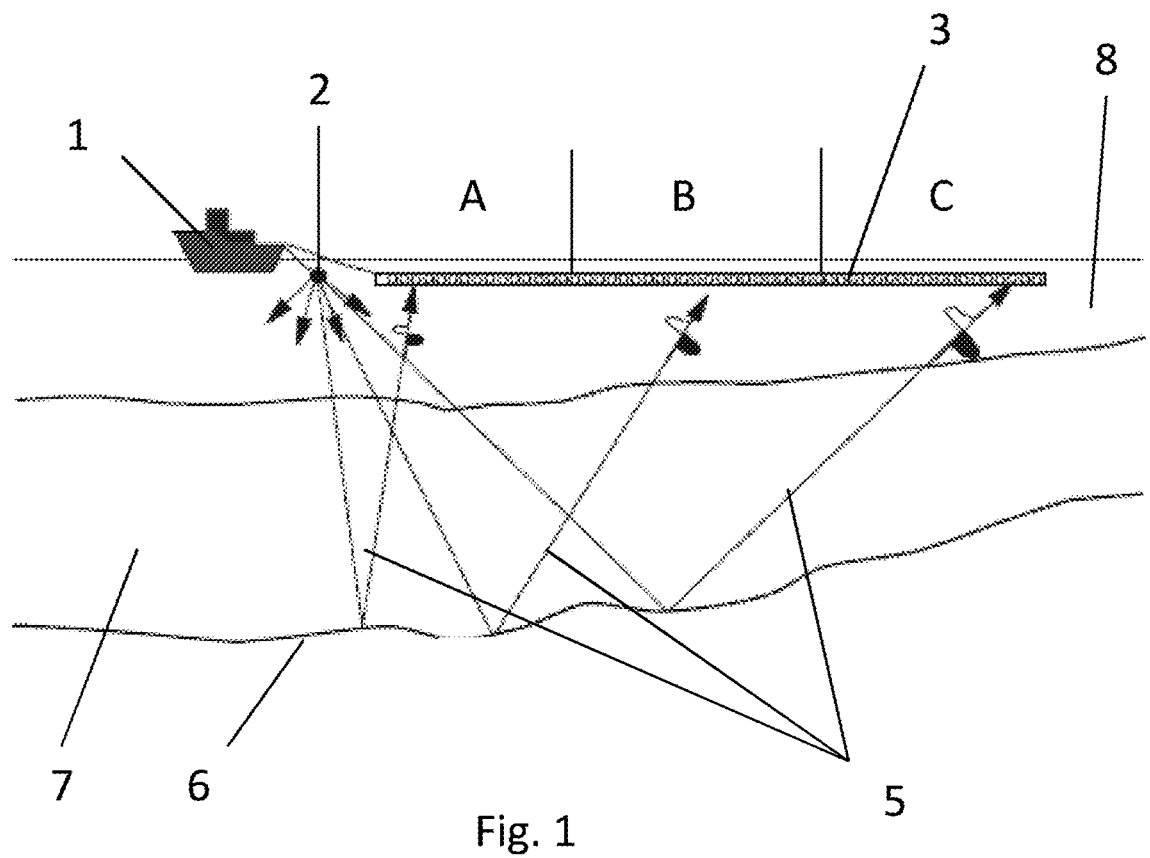
FIG. 1 is a schematic diagram illustrating the collection of near, mid and far stack seismic data with a seismic receiver array.

FIG. 1 illustrates a standard system which can be used to collect seismic data. However, any system which can be used to collect AVO seismic data can be used.

As shown in FIG. 1, a boat 1 tows a seismic source 2 and a seismic receiver array 3, across an area of water 8 and over a subsurface 7. The seismic source 2 is located in front of the seismic receiver array 3 in a towing direction.

In an embodiment, the seismic source 2 is an air gun. However, other kinds of seismic sources could alternatively be used.

The seismic receiver array 3 contains a plurality of seismic receivers located at different horizontal distances (offsets) from the source 2. In an embodiment, the seismic receiver array 3 is around 6 km long.

In operation, the seismic source 2 emits seismic waves which travel out from the source 2 down through the water 8 and the subsurface 7 and reflect off of a boundary 6 (reflector) in the subsurface 8. The boundary 6 is a reflective surface at which two different types of subsurface matter meet (e.g. hydrocarbon-saturated rock such as a sandstone reservoir, brine-saturated rock, rock impermeable to hydrocarbons such as shale, or rocks of different properties). For example, above the boundary 6 could be shale and below it could be an oilfield reservoir or hydrocarbon accumulation in a sandstone reservoir.

The reflected seismic waves, indicated by the arrows 5 in FIG. 1, are then detected by seismic receivers in the seismic receiver array 3 and recorded as seismic data. Such data is referred to as "pre stack" seismic data and is a measurement of reflection amplitude from the subsurface A (x, y, t, θ), where x and y represent the lateral position of the reflection point, t represents time, and θ is the angle of reflection at the reflector. The time t can be related to depth d by the equation:

$$t=2d/v \quad (1)$$

where v is the average velocity of the seismic waves in the subsurface from the seismic receiver to the reflector.

The receivers in the seismic receiver array 3 can be divided into three groups: a near group A, a mid group B and a far group C, as shown in FIG. 1. These groups A, B and C detect reflected seismic waves with increasing offsets from the source 2, which are equivalent to increasing angles of reflection. The seismic data detected at the groups A, B and C of receivers in the seismic receiver array 3 can be grouped (summed) into near, mid and far stack data, respectively.

The different stack gathers (e.g. near, mid and far) of seismic data can be analysed individually. They can alternatively or additionally be analysed in various linear combinations which can highlight different properties or features of the subsurface.

In a set of seismic data, there are typically a large number of measurements corresponding to the same reflection point (x, y, t) but with different reflection angles θ, where x, y, t and θ are defined above.

A common way to describe the angle dependent reflectivity with two terms is to calculate an intercept, IC, and a gradient, GR, by the finding the best fit to the equation:

$$A(\theta)=IC+GR*\sin^2(\theta) \quad (2)$$

where A is the total amplitude for a given reflection angle θ.

As shown in Whitcombe et al (2002), any linear combination between the intercept, IC, and the gradient, GR, can be described by the projection angle, χ, by the formula:

$$A(\chi)=IC*\cos(\chi)+GR*\sin(\chi) \quad (3).$$

A "fluid cube" is a seismic data cube where the angle χ is the fluid angle (typically around 15°) and a "lithology cube" is a seismic data cube where the angle χ is the lithology angle (typically around −45°). The fluid and lithology angles can be found theoretically from well logs or they can be estimated from the data itself, as is known in the art. A seismic data cube (or seismic cube) is a three-dimensional "image" of the subsurface giving the amplitude at all locations.

Both the IC and GR calculations, as well as the χ projections, are linear operators on the seismic data. In the simple case of a pre-stack dataset containing two angle stacks, near and far, representative of the reflection from two angles $\theta_N$ and $\theta_F$, respectively, the fluid cube and the lithology cube will both be simple linear combinations of the near and far stack data.

Consider the example where the near stack data (N) is at 10° (i.e. $\theta_N=10°$) and the far stack data (F) is at 30° (i.e. $\theta_F=30°$).

To find IC and GR using formula (2) gives:

$$N=IC+GR\sin^2(10°)$$

and $$F=GR*IC+\sin^2(30°)$$

Solving for IC and GR gives:

$$GR = (F-N)/[\sin^2(30°)-\sin^2(10°)]$$
$$= 4.54*(F-N)$$

$$IC = N - GR\sin^2(10°)$$
$$= N - \sin^2(10°)*(F-N)/[\sin^2(30°)-\sin^2(10°)]$$
$$= N - 0.137*(F-N)$$
$$= 1.137N - 0.137F$$

A fluid stack at χ=15° then becomes:

$$\text{Fluid} = IC^*\cos(15°) + GR^*\sin(15°)$$
$$= 0.966^*(1.137\,N - 0.137F) + 0.258^*4.54^*(F-N)$$
$$= -0.073^*N + 1.04\,F$$

which is a simple linear combination of N and F.

A key property of the fluid cube is that it is, from all of the possible χ angles, the cube that is the most sensitive to fluid changes in the reservoir. The lithology cube is the cube which is the least sensitive to fluid changes and thus only sensitive to lithology changes. The fluid cube will in general also be sensitive to lithology changes.

Thus, in an ideal situation with a reservoir of constant properties (where also the strata above and below the reservoir are constant), where the reservoir is inclined and oil-bearing at the top and water-bearing at the bottom, the fluid cube will show an amplitude change on the top and bottom reservoir crossing the contact between the oil and water-bearing regions, and the lithology cube will show no change.

As described above, once the seismic data has been obtained (step 20), the method involves defining or determining (for subsequent analysis) a set of tiles to be tested (step 21). As such, the software is written such that it defines small surface tiles of the seismic data cube, which typically each contain at least 40-100 traces, e.g. from 100 to 100,000 traces of seismic data. (A trace here is a curve describing seismic amplitude as a function of time, at one specific subsurface location. A seismic volume consists of a large number of traces, one for each subsurface location.)

In one embodiment, each tile contains 51×51=2601 traces.

The tiles can be any shape including square, rectangular, circular, elliptical or irregular in shape. In an embodiment, each tile has a central trace located at its centre. If the tiles are square or rectangular, then ideally they have an odd number of traces along each side, such that a central trace is located at the centre of the tile.

These surface tiles may be defined from a region of an already known horizon (a horizon typically represents a boundary that has been mapped from the seismic data by following a continuous pattern in the data, most typically a high positive or high negative amplitude) but tiles can also or alternatively be defined from a detection algorithm used to detect horizon tiles. If such a detection method is used, it does not necessarily need to detect a horizon in its full extent, only the small tiles. This means that the operation can be run in parallel for the tiles, as each tile is independent of the others.

One such horizon tile detection technique is that disclosed in GB 2429526. Another technique could be dip and azimuth and snapping, and another could be horizon tracking with the tile. Horizon tracking with the tile (an horizon autotracking technique) involves selecting a seed point trace and checking its correlation with neighbouring traces. If it is possible to follow a high amplitude in an area the size of a tile, then that area may be defined as a tile.

One method of identifying or defining tiles is as follows. First, a sub-cube is defined (selected) from a seismic data cube with the lateral size of a tile. A tile candidate in that sub-cube is selected with a depth and a dip (inclination of the plane measured in ms/m in two orthogonal directions). Then, all of the traces in the sub-cube are summed into a single trace along the dip. This is repeated for all tile candidates in the sub-cube (i.e. all dips and depths). A tile candidate is confirmed as a tile (i.e. corresponding to a possible boundary) if the sum shows a local maximum with respect to depth and dips. If confirmed, the tile is stored in a table in memory.

Figure 2:
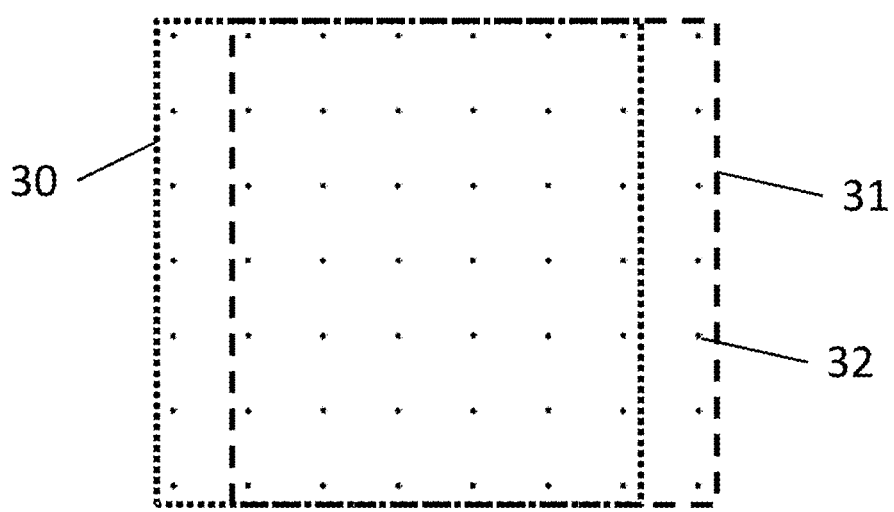
FIG. 2 is a schematic diagram illustrating two overlapping tiles.

The defined tiles have at least 50% overlap with adjacent tiles and, in some embodiments, close to 100% overlap. For example, in the case of square or rectangular tiles, adjacent tiles can overlap all traces except one (edge) row or column of traces. This is illustrated in FIG. 2, which shows two overlapping tiles 30 and 31, indicated by dotted and dashed lines, respectively. Each tile 30, 31 contains, as an example, an array of 7×7 traces 32 (each trace being indicated by a dot). It can be seen that tile 31 overlaps all but one column of the traces in tile 30, which corresponds to an 86% overlap.

In some cases, tiles are initially defined with around or close to 50% overlap and, if they are found to relate to an area of a possible fluid contact (following the steps described below), the tiles are re-defined with greater overlap (e.g. overlapping all except one column or row of traces of an adjacent tile) and the procedure repeated.

In one embodiment, the seismic data cube which is used as input for the part of the method in which the tiles are defined (detected) is a lithology cube (with a χ angle of around −45°) as this can align the tiles to the lithology of the subsurface and not be influenced by tuning effects that can affect the fluid cube at a fluid contact. However, the lithology cube can show little contrast and be prone to noise and thus difficult to use for initial detection. As such, in some embodiments, one seismic data cube (e.g. far stack or pseudo vp/vs stack) is used to define the tiles and another cube (e.g. the lithology cube) is used to determine its attributes (amplitudes), for subsequent analysis.

One embodiment, which is a preferred embodiment for a shale-sand system, uses a pseudo vp/vs cube (with a χ angle of around +45°) as input for the part of the method in which the tiles are defined (detected). As sand reservoirs typically have lower vp/vs than shale, sand reservoirs tend to be reflectors with the same polarity across fluids. For a fluid contact to be found, tiles need to be located such that they cross the fluid contact. If the amplitude changes so much across the fluid contact that it is, for example, a trough above the fluid contact and a peak below it, this will make the tile position itself incorrectly. A robust scheme is therefore needed for finding the top reservoir both in the oil and in the water zone of the reservoir, and the pseudo vp/vs cube is typically a good choice. As the pseudo vp/vs cube is not the lithology cube, it will be influenced by fluid effects, but typically not to an extreme extent. This makes it a good compromise for identifying the lithological boundaries of the subsurface.

Once the tiles have been defined, each tile is tested, at step 22, to assess whether or not it might correspond to a fluid contact. This is done by calculating the correlation between reservoir time (corresponding to depth) and (AVO) amplitude for that tile. The result is a quantitative measurement of local conformance with depth. If a high correlation is found, e.g. above 0.8, then that is indicative of the tile corresponding to a fluid-effect (i.e. a possible fluid contact).

Figure 3:
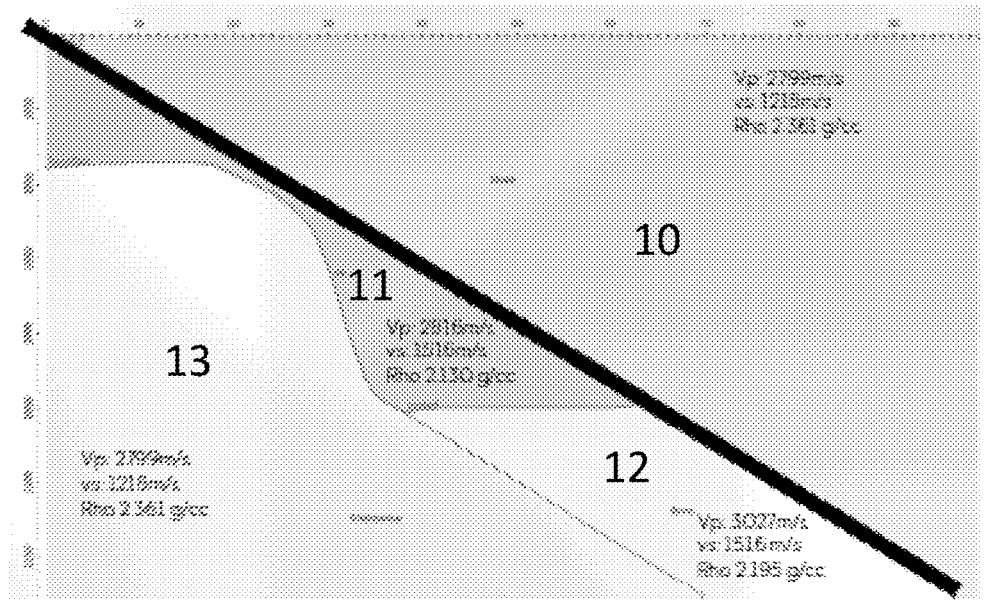
FIG. 3 is a graphical representation of a model of a subsurface.

FIG. 3 is a graphical representation of a subsurface model used in a simulation of seismic data to illustrate the present invention. The horizontal and vertical axes in FIG. 3 (and also in FIGS. 4A-E, which are described below) correspond to horizontal position and time, respectively, with time indicating depth. For simplicity and clarity, only two dimensions are shown. However, in practice the sub-surface would of course correspond to a three-dimensional region and data would be collected in three dimensions.

The sub-surface model of FIG. 3 contains four different regions. There are two solid regions: a first (upper) shale region 10 and a second (lower) shale region 13. There are also two fluid regions: an oil region 11 and a brine region 12. Together, the two fluid regions 11, 12 form an inclined reservoir with the oil region 11 at an upper end and the brine region 12 at a lower end.

FIGS. 4A-E graphically illustrate seismic data from different stacks from a simulation using the sub-surface model of FIG. 3.

Figure 4A:
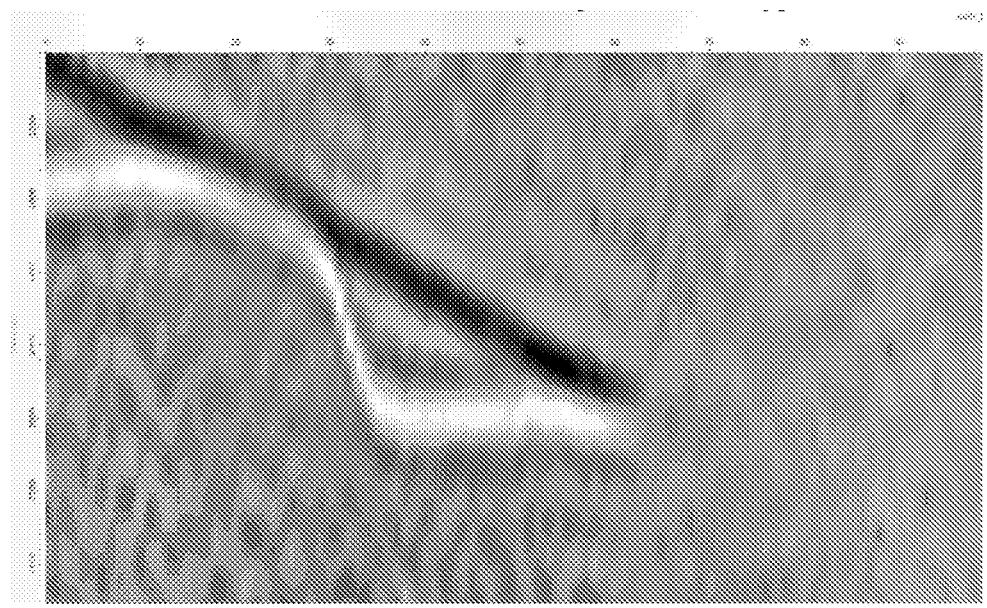
FIGS. 4A-E illustrate seismic data from different stacks from a simulation using the model of FIG. 3.

FIG. 4A shows simulated seismic data from a near stack with a mean angle of reflection of 10°.

Figure 4B:
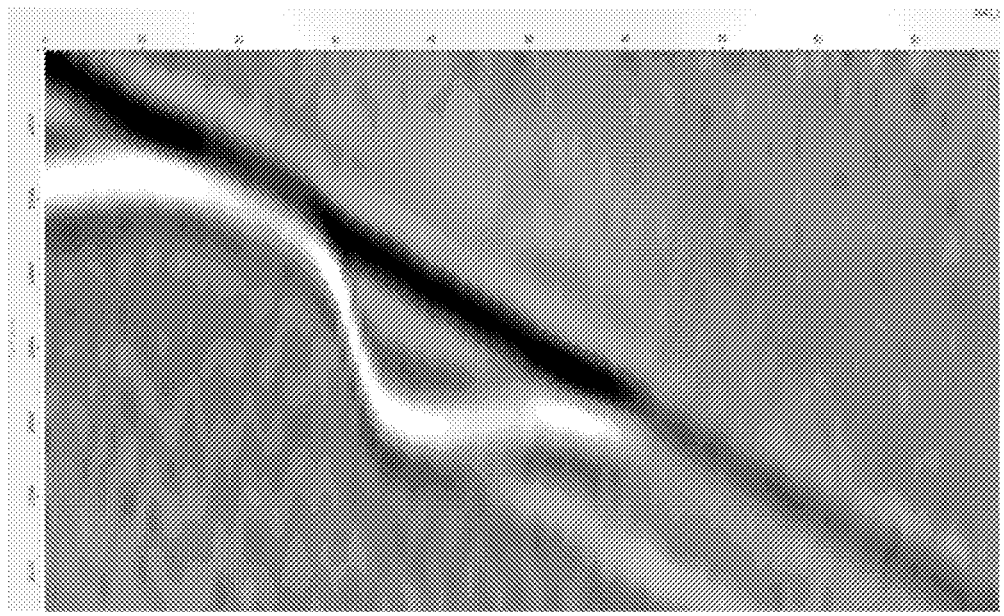

FIG. 4B shows simulated seismic data from a far stack with a mean angle of reflection of 30°.

Figure 4C:
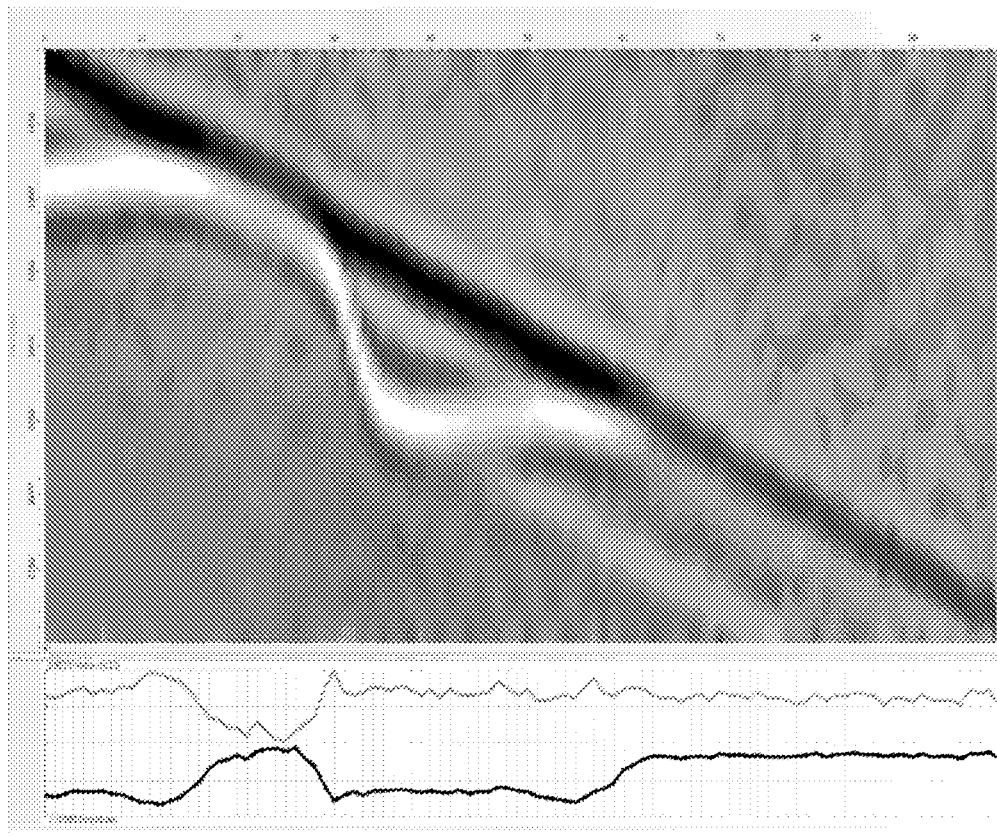

FIG. 4C shows simulated seismic data from a fluid stack with a $\chi$ value of 15°.

Figure 4D:
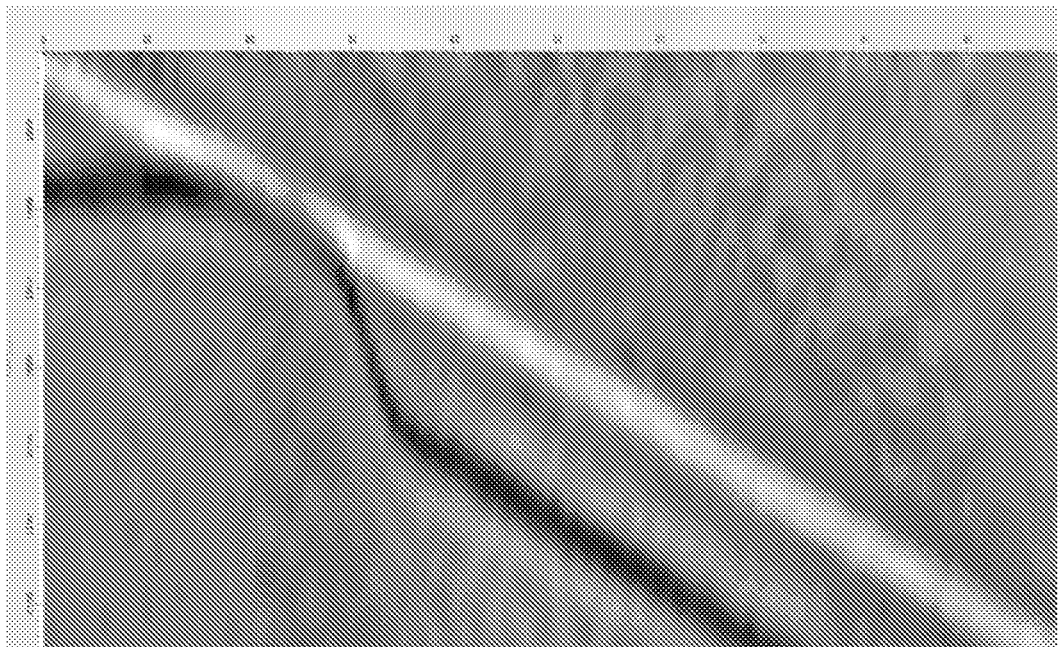

FIG. 4D shows simulated seismic data from a lithology stack with a $\chi$ value of −45°.

Figure 4E:
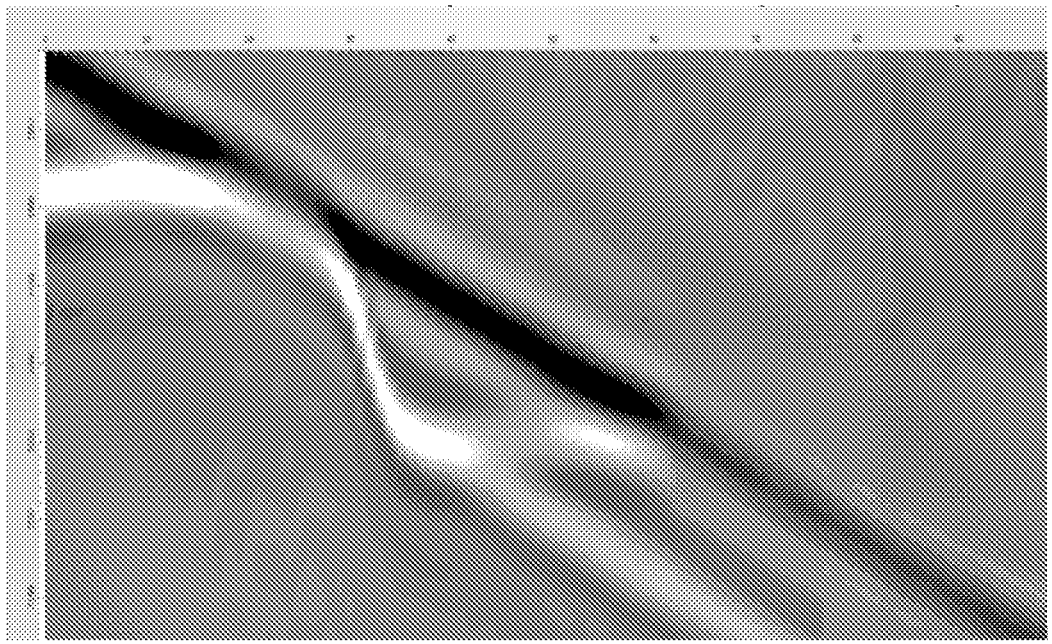

FIG. 4E shows simulated seismic data from a pseudo vp/vs stack with a $\chi$ value of 45°.

In FIGS. 4A-E, the darker the graph, the higher the amplitude detected from that point.

As can be seen from FIGS. 4C-E, in the lithology stack (FIG. 4D) there is no indication of the boundary between the two different fluid regions 11 and 12. However, in the fluid and pseudo vp/vs stacks (FIGS. 4C and 4E, respectively), this boundary is clearly visible.

FIG. 4C (the fluid stack) also shows that the fluid amplitude will shut off at a particular depth (or locally at a particular time on the seismic section, the seismic depth being measured in time as discussed above). This amplitude change will not be instantaneous but will show a linear trend around the time (depth) of the contact (between oil and brine/water). This effect is caused by the limited temporal resolution of the data, causing the amplitude at the top of the reservoir to be dependent not only on the fluid saturation immediately below the top of the reservoir, but also a small distance into the reservoir. The lateral extent of this zone of linear behaviour will depend primarily on the frequency content in the data and the dip (incline) of the reflector surface (i.e. the fluid contact).

In addition, there is a transition zone in saturation at the fluid contact (i.e. the reservoir does not abruptly change from oil to water, but this transition takes place over a region called the transition zone). Especially in the case of poor reservoir properties, there will be a gradual change from full saturation of one fluid phase to full saturation of the other fluid phase as a function of depth. This also contributes to making the transition in seismic reflection measured at the top reflection surface gradual.

As the amplitude change happens at around a specific seismic time (or depth), there is a strong correlation between the surface horizon time and the amplitude at the surface horizon. The correlation is strongest if the correlation is determined over the distance where the amplitude change is linear, but it will also be present if the lateral extent of the window (range) over which it is determined is larger. Thus, calculating the correlation coefficient between the time (depth) of the surface and the amplitude of the fluid attribute (amplitude) over a lateral window is a way of identifying whether there is a fluid contact in that window, as the correlation will be high. By using a window of constant size (thereby ensuring the same basis for statistics) and sliding the window across the section of interest, it is possible to identify a contact by the presence of a high such correlation.

This approach works even better when the correlation is done over a tile, where a tile is defined as a set of locations on the surface that are close in space, e.g. a rectangular, square, circular or elliptical area. The statistics of the correlation improve as more points (traces) are used.

Figure 10:
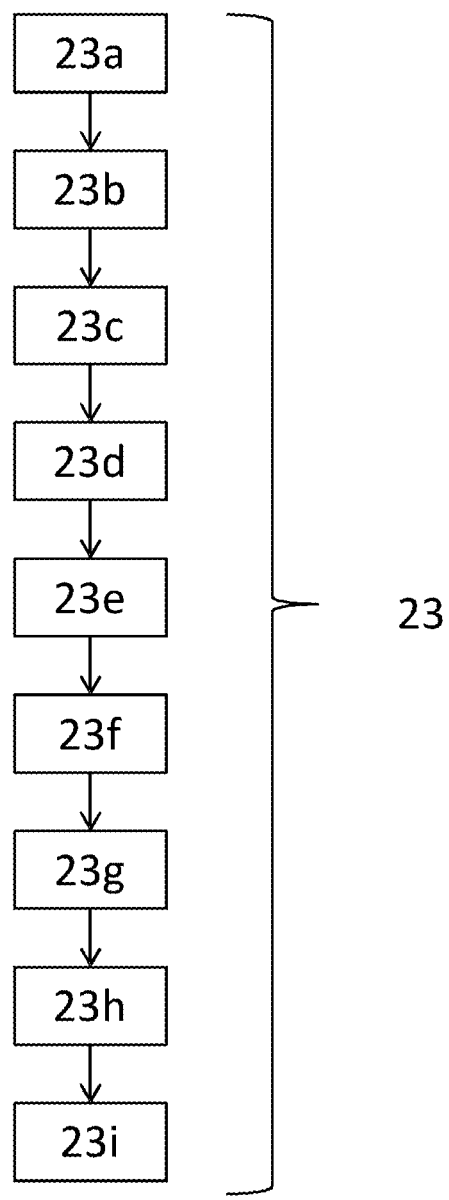
FIG. 10 is a flow chart illustrating a software method of performing further checks.

Once a tile has been identified as corresponding to a possible fluid contact, as described above, further checks can be performed to support or reject that identification, at step 23. Such further checks are now described below and illustrated in the flow diagram in FIG. 10.

The fluid cube is likely to show a high correlation between horizon time and horizon amplitude also in some cases not involving a fluid contact, such as cases where the sand quality is changing with time, either by chance or because of some depositional or diagenetic process. The presence of a high correlation between fluid amplitude and horizon time will thus not necessarily be sufficient by itself to discriminate between the effects set up by a fluid contact and other effects. However, in the ideal case with constant reservoir properties across the contact, the correlation between the lithology cube and the horizon time will be low. On the other hand, if the change is due to a lithology change, the correlation between the lithology cube and horizon time will also be high.

In view of the above, the method involves determining, at step 23a, whether a tile corresponds to a possible fluid contact by looking for both a high correlation between horizon time and fluid amplitude, as well as a low correlation between horizon time and lithology amplitude.

Figure 7A:
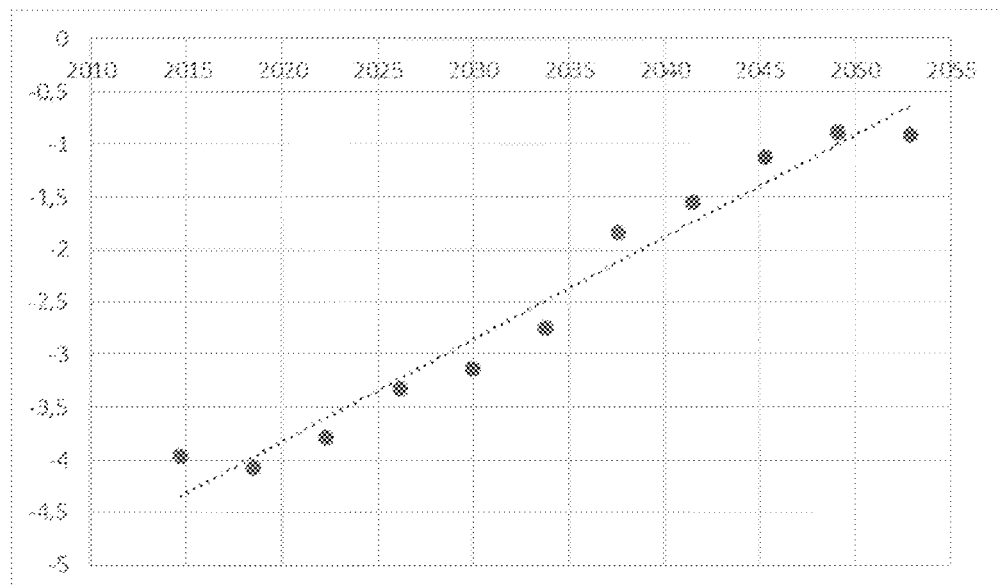
FIGS. 7A and 7B are graphs showing eleven traces of the fluid and lithology amplitudes, respectively, as a function of time.
Figure 7B:
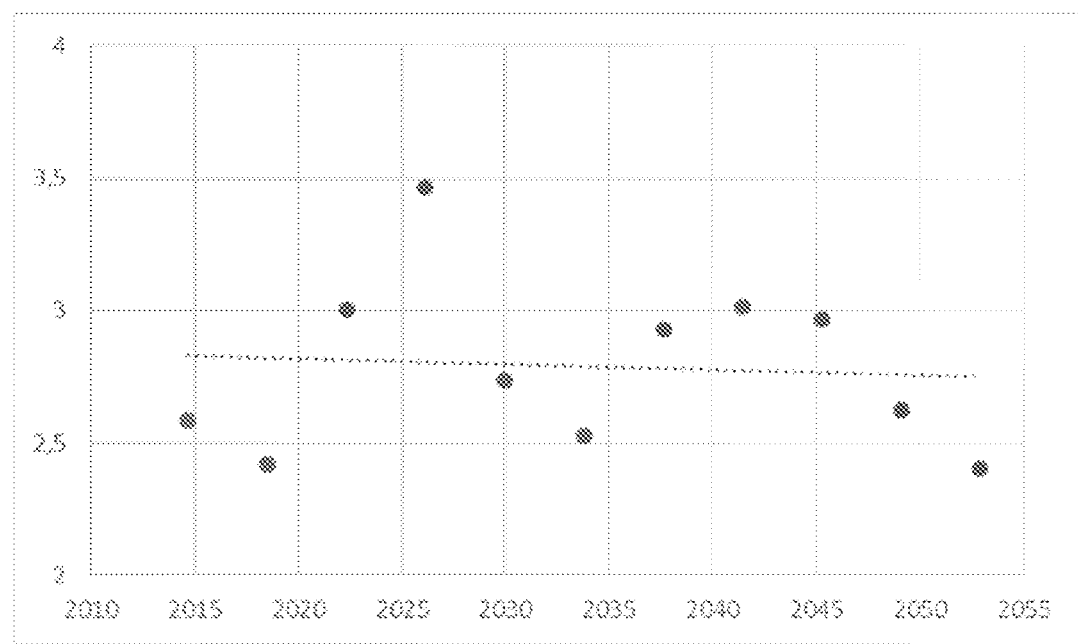

FIGS. 7A and 7B show graphs containing data from a tile of eleven traces with the fluid and lithology amplitudes, respectively, plotted as a function of time. FIG. 7A shows that, for this tile, the fluid amplitude correlates with time. The presence of this correlation suggests that this tile may be associated with a fluid contact. In addition, FIG. 7B shows that the lithology amplitude does not correlate with the time, which means that the fluid amplitude correlation is not caused by a lithology change, thus strengthening the case that this tile is associated with a fluid contact.

Figure 8A:
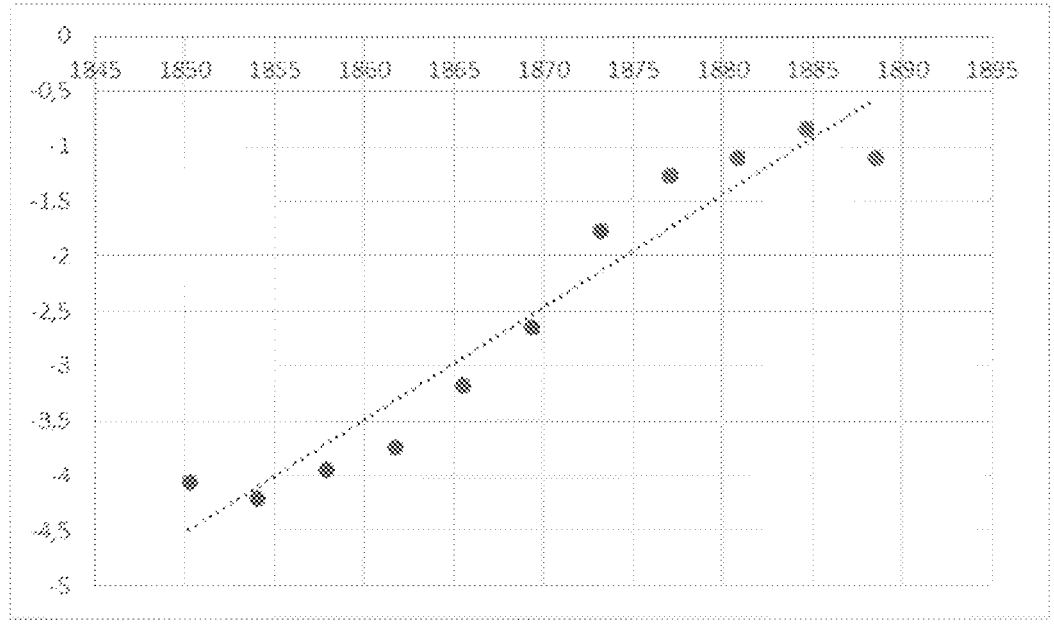
FIGS. 8A and 8B are graphs showing eleven different traces of the fluid and lithology amplitudes, respectively, as a function of time.
Figure 8B:
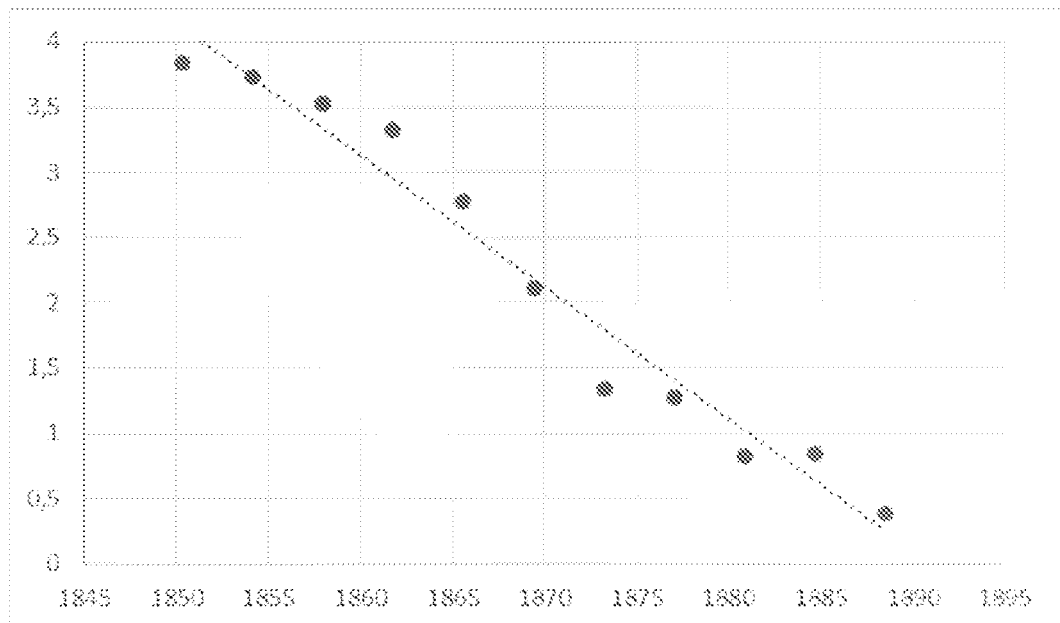

FIGS. 8A and 8B show graphs containing data from a different tile of eleven traces with the fluid and lithology amplitudes, respectively, plotted as a function of time. In this case, FIG. 8A shows that the fluid amplitude correlates with time, suggesting that the tile might be associated with a fluid contact. However, unlike the tile shown in FIGS. 7A and 7B, in this case FIG. 8B shows that the lithology also correlates with the time, which means that it is very likely that the reason for the correlation of fluid amplitude with time is a lithology change and not the presence of a fluid contact.

Figure 5:
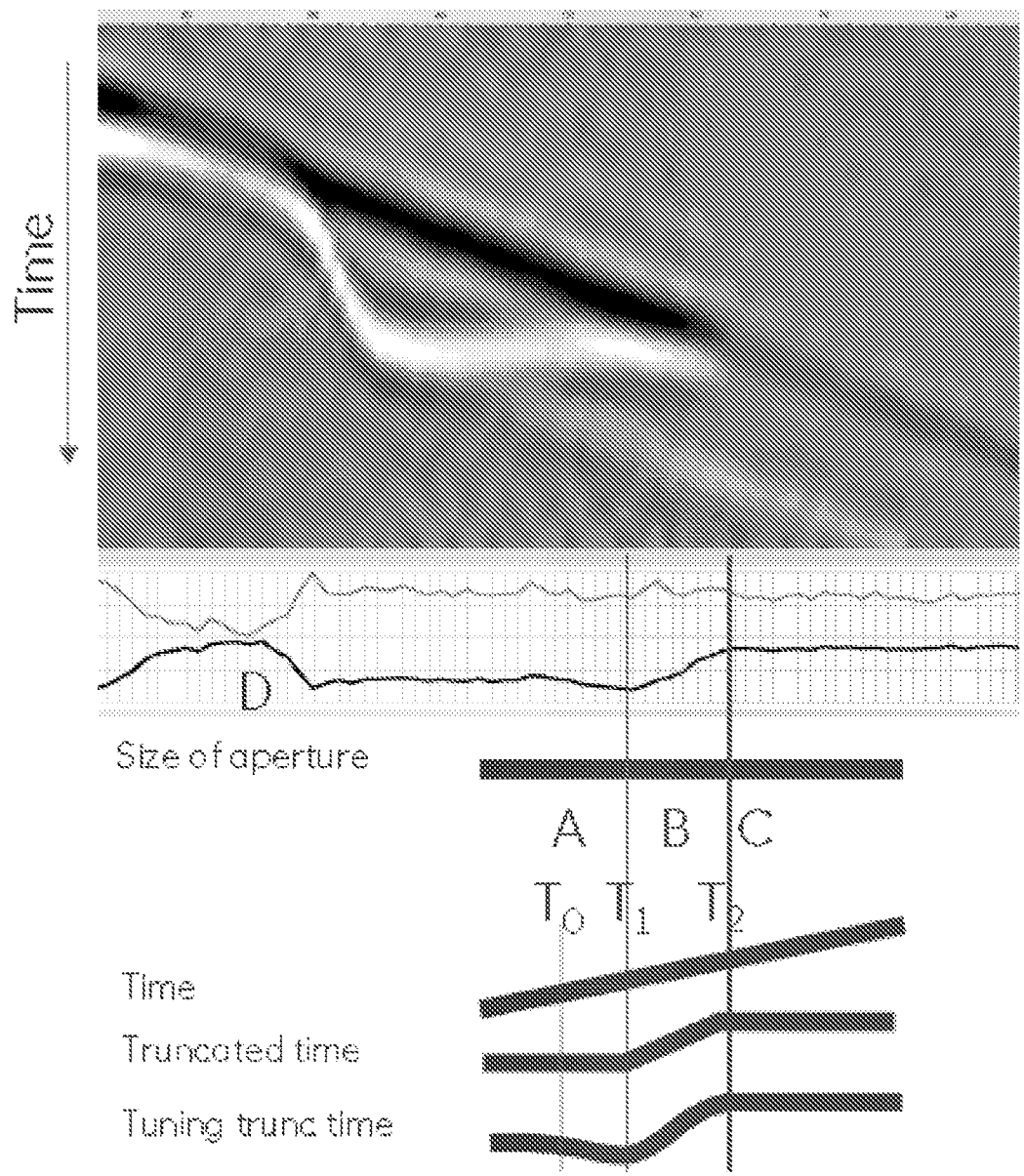
FIG. 5 is a graphical illustration of a clustering technique.

The x-axes of FIGS. 7 and 8 correspond to the y-axes of FIGS. 3 to 5.

Figure 9A:
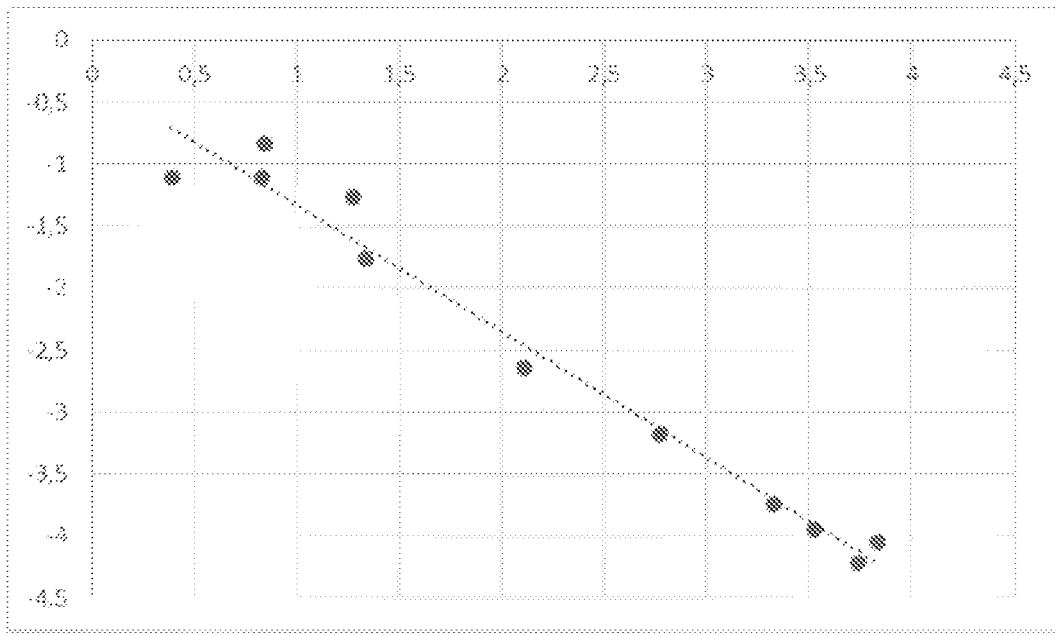
FIGS. 9A and 9B are graphs containing the same eleven traces as FIGS. 8A and 8B, and 7A and 7B, respectively, each showing the fluid amplitude plotted as a function of lithology amplitudes.
Figure 9B:
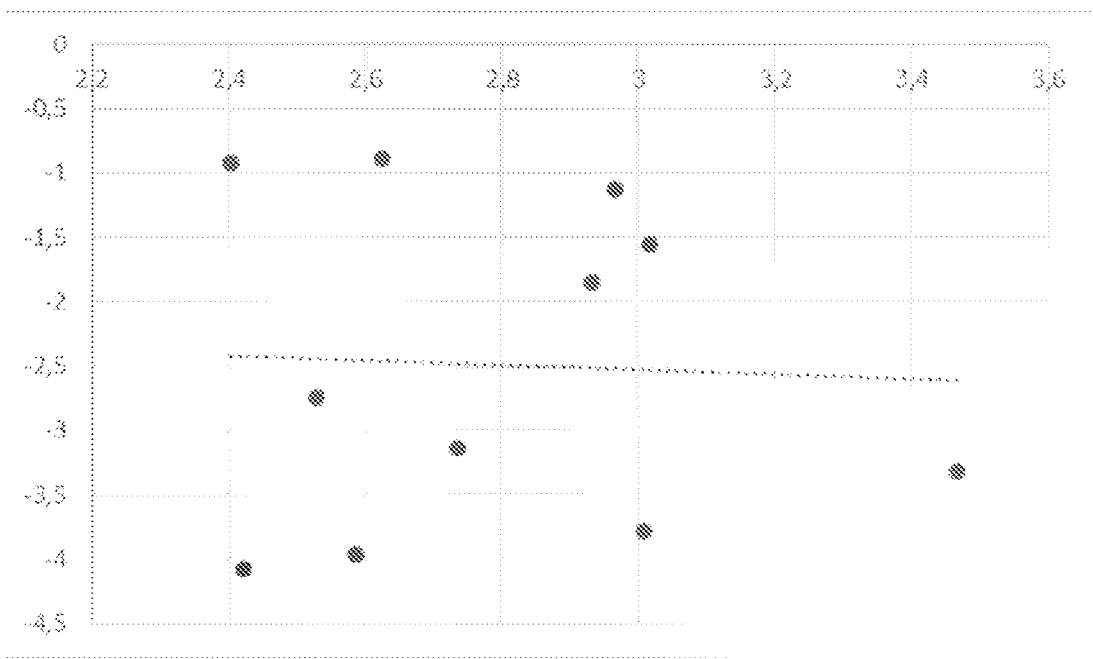

FIGS. 9A and 9B are graphs showing the fluid amplitude plotted as a function of lithology amplitude for the tiles shown in FIGS. 8A and 8B, and 9A and 9B, respectively. The values plotted in FIG. 9 correspond to those from the y axes of FIGS. 7 and 8. These amplitude values are arbitrarily scaled for illustrative purposes and are related to the darkness in FIGS. 2 to 4.

FIG. 9A, which shows the tile of FIGS. 8A and 8B, shows that the fluid amplitude correlates with the lithology amplitude. This suggests that reason for the fluid amplitude correlation seen in FIG. 8A is the lithology change and so the tile shown in these figures is not associated with a fluid contact.

FIG. 9B, which shows the tile of FIGS. 7A and 7B, shows that there is no correlation between the fluid amplitude and the lithology amplitude. Thus, the reason for the fluid amplitude correlation with time is not a lithology change and this strengthens the likelihood that this tile really is associated with a fluid contact.

The procedure for finding the base reservoir reflection is equivalent to the procedure of finding the top reservoir (surface) reflection. Depending on reservoir geometries and properties, it might not always be the case that there is a clear reflector that shows a fluid effect both at top and base. However, if both a top and a base reflection are found to exhibit a correlation between amplitude and depth at approximately the same depth, this further strengthens the hypothesis that this is related to a fluid contact. Thus, the method involves checking, at step 23b, for both a top and a base reflection exhibiting a correlation between amplitude and depth at approximately the same depth.

In a reservoir above a certain thickness, there will be a reflection from the fluid-fluid interface itself (a so-called flatspot), and a test can also be made, at step 23c, to check if this is the case, again strengthening the evidence of a fluid-fluid interface (a fluid contact) at that location.

The $\chi$ angles used to form the lithology and fluid stacks can vary a little from case to case, due for example to changes in reservoir properties and in seismic data quality. These changes are especially related to changes in amplitude between near and far stacks which are often found to be the case from, for example, overburden anomalies affecting the seismic ray-paths of the near and far stacks differently. This means that it can be difficult to know initially exactly which $\chi$ angle is best to use for each of the fluid and lithology stacks, respectively.

However, it is possible to calculate computationally the correlation between the time surface and all $\chi$ angles. Thus, the AVO character of a specific tile can be characterised by a function, referred to as Chicube, which is a correlation with time as function of $\chi$.

Due to the nature of the $\chi$ rotation:

$$\text{Chicube}(\chi) = -\text{Chicube}(\chi + 180°).$$

Thus, the Chicube curve is fully specified by knowing the values of $\chi$ between $-90°$ and $90°$, and Chicube $(90°) = -$ Chicube $(-90°)$.

By finding the maximum of Chicube, and the argument ($\chi$ value) at which this occurs, this gives the highest possible correlation obtainable, referred to as Corrmax, and the $\chi$ angle at which this occurs, $\chi_{max}$.

Assuming that Corrmax is non-zero (and as we are in general only interested in cases where Corrmax is large, this is fine), then the Chicube curve has to cross zero at some value $\chi_{min}$, because Chicube $(90°) = -$Chicube $(-90°)$.

The Chicube curve is generally smooth and slowly varying as a function of $\chi$, thus making the value $\chi_{min}$ single-valued and well-defined in the case of a reasonably high Corrmax. This indicates that it is possible to characterise this curve, and thus the AVO behaviour of the specific tile, by three variables, namely Corrmax, $\chi_{max}$, and $\chi_{min}$.

If Corrmax is high, $\chi_{max}$ is in a sensible fluid angle range and $\chi_{min}$ is in a sensible lithology angle range, then this is strong indication of the tile corresponding to a fluid contact. Thus, the method involves checking, at step 23d, that Corrmax is high, $\chi_{max}$ is in a sensible fluid angle range and $\chi_{min}$ is in a sensible lithology angle range. This approach is more robust to changes in the fluid and lithology $\chi$ angles.

Other tests such as standard deviation of lithology cube/ amplitude of fluid cube can also be applied to confirm or contradict the identification of a fluid contact.

For example, one test, performed at step 23e, involves determining the standard deviation of the lithology cube across the tile and then testing it in the following way. If this standard deviation is large, such as larger than the mean amplitude, this could indicate a large lateral variation in reservoir quality or that the tile is not aligned at all with a top reservoir but is crossing geological strata. This would give less confidence in a predicted fluid contact. If this standard deviation is low, such as less than the mean amplitude, then this would be strong evidence that the tile is correctly positioned on a "true" reflector and that the properties in terms of lithology are constant.

If the amplitude of the fluid cube is extremely weak compared to other amplitudes in the neighbourhood, for example less than 10% of other amplitudes, then this would be an indication that the amplitude relates merely to some noise or artefacts. Thus, the method involves checking, at step 23f, that the amplitude of the fluid cube is not significantly weaker than other amplitudes in the neighbourhood.

Once a tile has been identified as being a candidate for a fluid contact (i.e. by meeting the above criteria), it is possible to calculate other properties associated with the tile and to test those properties. For example, at step 23g, the ratio between the standard deviation of the lithology attribute (amplitude) and the mean of the lithology attribute (amplitude) is determined and tested in the following way. Low values of this ratio, e.g. less than 0.5, would indicate that the lithology is fairly constant in the tile, which would further strengthen the case that the tile is associated with a fluid contact, whereas high values of this ratio, e.g. greater than 1, would indicate that the lithology is varying strongly in the tile, potentially due to noise or other issues, and that the measurement of correlation is to be trusted less.

A measurement other than the Pearson correlation coefficient could also or alternatively be used to assess the likelihood of the tile being associated with a fluid contact. For example, a measurement that would return high values also in a situation where the correlation window is significantly larger, so that the time interval covered would exceed the range of linear amplitude, could be used.

Truncating the time value to a constant at high and low times, such as outside a constant time range centred around the mean or median time of the surface (tile), where the time range is related to the frequency content in the data, can make the method more robust for larger windows (tiles). Other such measures are also possible, such as taking the tuning effect at the contact into account. This is illustrated in FIG. 5.

It can be beneficial to use a large aperture or tile size, for example in a situation with noisy data where the detection of the structure itself requires a large aperture, or where a lot of spurious correlations are found for small apertures (tile sizes). The probability of a "false" correlation (i.e. a large correlation which does not actually correspond to a fluid effect) is proportional to $1/\sqrt{N}$, where N is the number of traces.

However, in such a situation the size of the aperture might be much larger than the area where the relationship between time and amplitude is linear. This is illustrated in FIG. 5, where the aperture consists of areas A, B and C, but the relationship between time and amplitude is only linear in area B. $T_0$, $T_1$, $T_2$ and the truncated time curve are shown on the x-axis of the plot. They are really properties that belong on the y-axis but as the model has a simple linear relationship between x-axis and time, this is valid in this example.

By replacing correlation as the measurement, with a measurement that divides the aperture into three areas or clusters, A, B and C, separated by times $T_1$ and $T_2$, it is clear that the criterion (for a fluid contact to be identified) could be that within areas A and C fluid amplitudes should be relatively constant if the lithology amplitude is constant (but the level of fluid amplitude in area A should be different from that of area C) whereas a linear trend should be present in area B.

One very simple way of implementing this is to estimate the time window of the transition zone ($T_{trans}=T_2-T_1$) and then for each tile calculate the mean T value ($T_{mean}$) and truncate all times outside of the transition window such that if $T>T_{mean}+T_{trans}/2$ then $T=T_{mean}+T_{trans}/2$ and if $T<T_{mean}-T_{trans}/2$ then $T=T_{mean}-T_{trans}/2$ This would give a correlation close to 1 in the situation shown in FIG. 5.

Due to tuning effects, the amplitude as function of height above the fluid contact is expected to show a maximum at a specific hydrocarbon thickness (height), as seen in $T_1$, and then decrease slightly as the thickness increases. In the "tuning trunc time" curve in FIG. 5, the value at $T_1$ is the lowest of all values between $T_0$ and $T_2$. This is the tuning effect, i.e. that the curve seen slightly to the left of $T_0$ going to the right (i.e. towards a thinner layer) goes to a maximum of negative amplitude at a given thickness, before dying off towards zero. This effect is seen in real data. Including this could therefore improve the measurement, i.e, by using a correlation with "tuning trunc time" (tuning truncated time) as shown in FIG. 5.

It is possible to do this in a more general way and use a computer algorithm to find the optimal parameters, as they can vary with lithology properties. In one embodiment, the "tuning trunc time" curve is parameterized with a function $T'=f(T, T_0, T_1, T_2)$. The variables $T_0, T_1, T_2$ are then scanned over to select those giving the highest value of correlation between the fluid cube and T'.

It is also possible, e.g. in some embodiments, to use the fact that the fluid cube correlates with the lithology cube to make a measurement that is robust for this correlation, i.e. to not "punish" the measurement in a situation where the aperture is so large that is also includes a further area D, where there is no correlation. In an ideal case there is a very high correlation between fluid and lithology attributes. Techniques such as machine learning can be used in this situation, for example to feed in the lithology attribute, the fluid attribute and the time surface, and to return the probability of a fluid contact, and possibly the time of the fluid contact.

In some embodiments, two distinct fluid contacts are looked for, in which case the method is extended to look for this by extending the number of clusters.

In some embodiments, a refinement step 23*h* is performed when a potential contact tile has been identified. This refinement step searches for an optimum size and/or shape of the tile to correlate over, where the optimum tile size and/or shape is chosen to be that with the highest correlation or some other measurement involving correlations.

The algorithm described above will typically not only identify true positives, e.g. tiles representative of true geological boundaries crossing a fluid contact, but also a number of false positives, e.g. tiles that show a high score, but in reality do not represent a geological boundary crossing a fluid contact. The occurrence of such false positives could be caused by artefacts such as noise, for example. If the number of false positives is high compared to the number of true positives, this will negatively impact the value of the method. If, for example, there is one true positive in a dataset, but the method returns this together with 100 false positives, the true positive might be overlooked. If, on the other hand, there are only five false positives, it is likely that all six positives will be put under manual scrutiny such as to reveal the true positive. In practice, the positives may be ranked with a score, related to the size and number of indications of being a fluid effect. A true positive should be relatively close to the top of the ranked list to be detected manually. If, for example, a positive is in around the top ten of the ranked list, it is likely that it would still be found by manual scrutiny, whereas it is unlikely that such a positive would be found if it were below the top 100.

Because of this, it is, e.g. under typical circumstances of relatively weak fluid effects, strong noise and thus a considerable number of false positives, necessary or highly desirable to include tests to remove as many of the false positives as possible. In practice, a scheme for defining such tests may be done by manually investigating a tile with a high score, determining if it is a true or false positive, and finding some attribute that can be used to distinguish the false from the true positive. This attribute may then be calculated automatically for all tiles, and the process may be repeated to obtain a set of attributes. Some attributes that may be helpful, in addition to those already mentioned, are described below.

The mean amplitude of the fluid attribute divided by the standard deviation of the same may be a helpful attribute to determine and use. The amplitude of the fluid cube is usually expected to be negative in the cases of both hydrocarbons and brine. Thus, the mean value of the amplitude is expected to be negative, and the mean divided by the standard deviation should be less than −1 if most values are negative. This test will therefore allow the removal of false positives related to positive fluid amplitudes that are typically not caused by hydrocarbons.

If a false positive is related to a tile that is not a geological reflector, but rather to noise, the result could be a tile that has a dip very different from the local prevailing dip. Such tiles may be filtered out by checking for the local prevailing dip, which is found from the dips of the tiles in a local neighbourhood. A local neighbourhood here may comprise or consist of the tiles which are at the same lateral position and a time less than 100 ms above or below that of the tile in question, for example. If most of the tiles in the local neighbourhood with relatively high amplitudes (for example more than 150% of that of the fluid effect candidate amplitude) have significantly different dips (for example more than two discretisation dip steps in at least one dip direction, a dip discretisation step typically being sqrt(3)/Rx in units samples in vertical (depth or time direction) over samples in lateral direction, and Rx is half of the size of the tile in the lateral direction) to that of the candidate for a fluid effect tile, then the fluid effect tile may be regarded or labelled as a false positive.

In addition, false positives are typically not part of continuous reflector surfaces that extend in all directions. This can be tested for by checking if the tile in question lines up with neighbouring tiles. If, from a potential fluid effect tile it is not possible to make a continuous patch of connected tiles consisting of a minimum number of tiles, e.g. 4, 8 or 40, or the potential fluid effect tile has fewer than four nearest neighbours (of four possible, counting in each of the four main directions), then the potential fluid effect tile can be regarded or labelled as a false positive.

A hydrocarbon accumulation of an economically interesting (large) size is likely to cause a large number of true positive fluid effect tiles. Such an effect will be present both on the top and base reservoir reflectors, and also on internal reservoir reflectors in the event of a thick reservoir. If the accumulation is relatively large in size, and the reflectors are broken up, e.g. by faults or poor data quality areas, even a reflector that is geologically the same surface, e.g. the top reservoir surface, may be seen by the algorithm as separate surface patches. For these reasons, a hydrocarbon accumulation of an economically interesting size will tend to show a large number of fluid effect tiles, spread over a number of surface patches. By grouping surface patches that show evidence of fluid effects (by containing one or more tiles showing a fluid effect), based on their proximity in space, into a patch collection, it is possible to apply metrics on such collections, to be able to rank these according to size and probability of a true fluid effect. Some attributes of such collections may include: the total number of tiles in the collection, the number of tiles that show a fluid effect, and how well the fluid effect tiles line up at a specific time/depth, measured, for example, by a histogram over fluid tiles as function of time/depth. Each patch in the collection may be tested to see if the amplitude changes in the collection are consistent also on larger scale than in the individual tiles.

When a tile has been identified, filters can be applied not only using the attributes related to the particular tile itself, but also by demanding, at step 23i, that several tiles should line up around the contact (i.e. there should be a plurality of tiles in a row all having been identified as being associated with a fluid contact), such as is expected for a fluid contact covering a large area. In a real situation one would expect that only part of the contact is found in constant lithology, thus it would be possible to use one or a few tiles that exhibit a correlation with fluid and no correlation with lithology to validate a connected chain of tiles that show also some correlation with structure. This can be expanded to also look for correlation of time and amplitude at internal reflectors and base reflectors, as well as flatspots, and then assign to the detected surfaces with multiple observations a higher likelihood of corresponding to a fluid contact.

As can be appreciated from the above, there are various ways in which a tile can be checked to determine whether or not it corresponds to a fluid contact.

These checks (e.g. the steps 23a-23i of FIG. 10 and/or described above) can be performed in any order.

In some embodiments, all of these checks would be performed.

In some embodiments, only a selection (one or more) or these checked would be performed.

In some embodiments, if one or more checks suggest that the tile does not correspond to a fluid contact, then that tile is not identified as corresponding to a possible fluid contact.

In some embodiments, a tile must "pass" all checks in order to be identified as corresponding to a possible fluid contact.

In some embodiments, a tile must "pass" at least a certain number of checks in order to be identified as corresponding to a possible fluid contact.

In some embodiments, one or more checks are designated as "fundamental" checks and if a tile fails one of those fundamental checks then it is not identified as corresponding to a possible fluid contact.

Once fluid effect tiles have been identified (i.e. tiles associated with a possible or probable fluid contact) they can be saved in memory (e.g. the locations of the tiles with an associated probability of the tile being associated with a fluid contact) at step 24 and/or displayed graphically, e.g. on a computer screen, to show where possible fluid contacts are.

If any new locations of possible hydrocarbons are identified, then a decision may be made about whether or not to drill for hydrocarbons at that location (e.g. based on other factors). If it is decided to drill for hydrocarbons at that location, a drill may be installed and hydrocarbons may then be drilled for at that location.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

REFERENCE

David N. Whitcombe, Patrick A. Connolly, Roger L. Reagan, and Terry C. Redshaw, "Extended elastic impedance for fluid and lithology prediction", Geophysics Vol. 67, No. 1 (January-February 2002), pp 63-67.

We claim:

1. A method of prospecting for hydrocarbons, the method comprising:
analysing seismic data to determine a possible location of hydrocarbons by determining a set of data tiles from a seismic data cube of seismic data; and
testing each data tile in the set of data tiles to determine whether it corresponds to a possible fluid contact;
wherein determining a set of data tiles from a seismic data cube of seismic data comprises:
(i) defining a sub-cube with a lateral size of a tile and comprising a plurality of traces;
(ii) selecting a tile candidate in the sub-cube, the tile candidate having an associated depth and dip;
(iii) summing all of the traces in the sub-cube into a single trace along the dip;
(iv) repeating steps (ii) and (iii) for all tile candidates in the sub-cube;
(v) confirming a tile candidate as a tile if the summed single trace shows a local amplitude maximum with respect to depth and dips; and
(vi) if a tile candidate is confirmed as a tile, storing the tile in a memory;
the method further comprising:
outputting a set of possible locations of hydrocarbons corresponding to one or more locations of fluid contacts; and
drilling for hydrocarbons at at least one of, or at a location within, the output set of locations.

2. A method as claimed in claim 1, wherein the seismic data comprises pre-stack seismic data.

3. A method as claimed in claim 1, wherein the seismic data cube from which the set of data tiles are determined is a seismic data cube suitable for identifying seismic lithology reflections; and/or the method comprises obtaining a seismic data cube suitable for identifying seismic lithology reflections from the seismic data.

4. A method as claimed in claim 1, wherein the set of data tiles comprises tiles which are representative of a lithology change in the subsurface.

5. A method as claimed in claim 1, wherein each data tile in the set of data tiles comprises or corresponds to a lateral area of more than 40 or preferably more than 400 seismic traces.

6. A method as claimed in claim 1, wherein testing each data tile in the set of data tiles to determine whether it corresponds to a possible fluid contact comprises determining a correlation between amplitude and time for each tile.

7. A method as claimed in claim 6, wherein testing each data tile in the set of data tiles to determine whether it corresponds to a possible fluid contact comprises, for each tile:
   obtaining a plurality of measurements representative of reservoir properties at each of the locations in the tile or of the average properties in a depth window above and/or below the tile; and
   calculating a degree of co-variation between a plurality of such measurements and the measured time or depth of the tile.

8. A method as claimed in claim 7, wherein the measurements representative of reservoir properties at each of the locations in the tile or of the average properties in a depth window above and/or below the tile show different sensitivities to reservoir fluids.

9. A method as claimed in claim 7, further comprising performing a cluster analysis on the measurements representative of reservoir properties at each of the locations in the tile or of the average properties in a depth window above and/or below the tile to identify how well traces in the data tile can be separated into a plurality of clusters.

10. A method as claimed in claim 9, wherein a time or depth of each trace is used as a means to separate the clusters.

11. A method as claimed in claim 10, wherein the plurality of clusters consists of:
   two clusters and the time or depth that separates the clusters corresponds to that of a fluid contact; or
   three clusters and two times or depths are used to separate the clusters, the two times or depths representing those of a top and a base, respectively, of a transition zone of relatively linear dependency of depth or time and fluid-effect amplitude; or
   three or more clusters and the times or depths that separate the clusters correspond to those of a plurality of fluid contacts and/or transition zones.

12. A method as claimed in claim 7, wherein the degree of co-variation is the Pearson correlation coefficient.

13. A method as claimed in claim 7, wherein the measurements representative of reservoir properties are from $\chi$ angle rotations.

14. A method as claimed in claim 7, further comprising identifying tiles that show a relatively high co-variation of a fluid-sensitive measurement and the tile time or depth and/or a relatively low co-variation of a less fluid-sensitive measurement and the tile time or depth.

15. A method as claimed in claim 1, further comprising applying a filter to identify only tiles that line up with other tiles to form a larger structure above a certain size as corresponding to a possible fluid contact.

16. A method as claimed in claim 1, the method comprising obtaining the seismic data from a memory or acquiring the seismic data with at least one seismic source and at least one seismic receiver array.

17. A method of prospecting for hydrocarbons comprising performing the method of claim 1 and using the output set of locations in the decision-making process for the drilling of a well.

18. A computer program product comprising computer readable instructions that, when run on a computer, is configured to cause one or more processors to perform the method of claim 1.

* * * * *